United States Patent [19]

Mauzac et al.

[11] Patent Number: 4,740,594

[45] Date of Patent: Apr. 26, 1988

[54] DEXTRAN DERIVATIVES ENDOWED, PARTICULARLY WITH ANTI-COAGULANT PROPERTIES AND ANTI-COMPLEMENTARY PROPERTIES, THEIR PREPARATION AND THEIR BIOLOGICAL USES

[75] Inventors: Monique Mauzac, Gujan Mestras; Jacqueline Jozefonvicz; Marcel Jozefonvicz, both of La Morlaye, all of France

[73] Assignee: Choay S.A., Paris, France

[21] Appl. No.: 676,649

[22] Filed: Nov. 30, 1984

[30] Foreign Application Priority Data

Nov. 30, 1983 [FR] France .................. 83 19110

[51] Int. Cl.$^4$ .................. A61K 31/70; A61K 31/725; C08B 37/02
[52] U.S. Cl. .................. 536/51; 536/53; 536/112; 514/832; 514/833
[58] Field of Search .................. 536/112, 53, 51; 514/59, 832, 833

[56] References Cited

U.S. PATENT DOCUMENTS

| | | | |
|---|---|---|---|
| 2,216,617 | 10/1940 | Katz | 536/53 |
| 2,989,518 | 6/1961 | Novak | 536/112 |
| 4,411,891 | 10/1983 | Mizutani et al. | 514/59 |
| 4,591,638 | 5/1986 | Ahrgren et al. | 536/51 |

Primary Examiner—Ronald W. Griffin
Attorney, Agent, or Firm—Weiser & Stapler

[57] ABSTRACT

The dextran derivatives have a molecular weight higher than about 5000 daltons and comprise statistically at least about 35% of units substituted by radicals having a COO$^-$ function and at least 3% of units comprising a group of structure

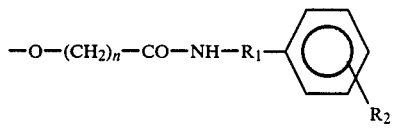

wherein $R_1$ is a single bond; or a

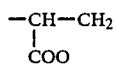

group, $R_2$ is an anion of an inorganic or an organic salt and n is a number from 1 to 4.

26 Claims, 4 Drawing Sheets

DEXTRAN DERIVATIVES ENDOWED, PARTICULARLY WITH ANTI-COAGULANT PROPERTIES AND ANTI-COMPLEMENTARY PROPERTIES, THEIR PREPARATION AND THEIR BIOLOGICAL USES

BACKGROUND OF THE INVENTION

The invention relates to derivatives of dextran endowed, particularly with anti-coagulant properties and anti-complementary properties, to their preparation and to their biological uses.

It is known that heparin is widely used as an anti-thrombotic medicament by reason of its high anti-coagulant properties.

Recent work has also shown its action with respect to the inactivation of the complementary system, that is to say the group of plasma proteins playing an essential role in the immunitary defence of the organism.

The heterogeneity of its chains, particularly, as regards their composition and their length, renders however difficult study of the structures responsible for its properties.

Numerous researches have been undertaken to develop products having at least certain of the specific properties of heparin, but of well-defined structure thus capable of serving as a model for the study of the corresponding mechanisms brought into play.

Some of the co-inventors of the invention have prepared and disclosed (FR Pat. No. 2 461 724 and EP patent application No. 80 401053.6) compounds having anti-coagulant properties, consisting of polymers having the following groups:

wherein $R_1$ is an hydrogen atom or a physiologically acceptable metal $R_2$ is an aminoacid residue bound to $-SO_2-$ through an amino function $R_3$ is a $-CH_2-CO-NH-R_4$ group wherein $R_4$ is a substituted or unsubstituted alkyl, arly or aralkyl or radical and R represents the branched chain on an aminoacid.

The researches of the Applicants in this field has brought them to study a polysaccharide already known, namely dextran.

Dextran is a polyglucoside of molecular weight from about 5000 to several millions of daltons, formed by glucosyl units A with linkages essentially of the 1-6 type of the formula:

In the therapeutical uses, dextrans having molecular weights less than about 100,000 are generally used.

Dextran is used particularly, as a blood plasma substitute or at least as an expander. These uses can result however, in certain cases, in immunitary shocks.

The studies carried out have shown that the simultaneous presence of certain substituent groups, in predetermined proportions, on dextran chains free of aminoacids, confered to the dextrans biological properties of great interest and high tolerance.

Accordingly it is an object of the invention to provide derivatives of dextran having at least certain of the biological properties of heparin and useful as biomaterials due to their high tolerance.

It is also an object of the invention to provide a process for the preparation of these derivatives which is easy to put into practice.

It is equally an object to provide soluble biomaterials and medicaments or vectors of medicaments of high efficiency based on these derivatives having the advantage of being obtained synthetically.

GENERAL DESCRIPTION OF THE INVENTION

According to the invention there are provided dextran derivatives characterized in that they possess a molecular weight higher that about 5000 daltons, and that they comprise statistically, at least about 35% and more particularly at least about 40% of B units, i.e. units substituted by radicals possessing a carboxyl function, corresponding to the structure $-O-(CH_2)_n-R-COO^-$ in which R represents a single bond or a $-CO-NH-(CH_2)_{n'}-$, n is a number from 1 to 10 and n' is a number from 1 to 7, and at least about 3% of D units i.e. units substituted by a chain comprising a group of structure in which:

$R_1$ represents a single bond, $-CH_2-$ group, or a group, $R_2$ represents a physiologically tolerance anion of an inorganic or organic salt, especially an $SO_3^-$ group, and n is as defined above.

The functionalization of the dextran support by means of a substituent chains defined above confers advantageously on this latter dextran, an anticoagulant activity. This activity, although lower than that of heparin, has great interest for biological applications of these derivatives.

These products appear, moreover, to be endowed with an anti-complementary activity of the same order of magnitude as that of heparin.

It will be observed that the advantageous effects are obtained by the simultaneous presence (1) of carboxyl groups on the B units and (2) substituent chains on the D units, comprising aryl groups substituted by an anion of an inorganic or organic salt and more especially arylsulfonate groups, and linked to the dextran chain by an arm comprising an amide group.

According to an advantageous feature of the invention, the dextran derivatives contain moreover C units substituted by radicals of structure $$-O-(CH_2)_n-CO-NH-R_1-\langle\bigcirc\rangle,$$

in which $R_1$ and n are as defined above.

All of the unsubstituted A units of the dextran and of the above C units represent at the most 60% of the total number of units.

The preferred family of dextran derivatives, according to the invention, comprises B units substituted by a $-O-CH_2-COO^-$ chain.

In another family of the invention, the B units are substituted by carboxyethyl, carboxypropyl or carboxybutyl $-O-(CH_2)_n-COO^-$, n being equal respectively to 2, 3 or 4.

According to another preferred family, the B units are substituted by $-O-(CH_2)_{n'}-CO-NH-(CH_2)_{n'}-COO^-$.

The derivatives in which n' is equal to 4, 5 or 7 comprise a $-NH-(CH_2)_{n'}-COO^-$ radical corresponding respectively to a valeric acid, aminocaproic acid and aminocaprylic acid group.

A preferred group of dextran derivatives of the invention contains, at the same time as the B units of one of the above-defined families, D units substituted by a chain of structure $$-O-(CH_2)_n-CONH-\langle\bigcirc\rangle_{R_2}$$

In another preferred group, the dextran chains contain in addition to the above B units, D units substituted by chains of structure $$-O-(CH_2)_n-CO-NH-CH_2-\langle\bigcirc\rangle_{R_2}$$

In another group also, the D units are substituted by chains of structure $$-O-(CH_2)_n-CO-NH-CH-CH_2-\langle\bigcirc\rangle_{R_2}$$
$$\quad\quad\quad\quad\quad\quad\quad\quad\quad |$$
$$\quad\quad\quad\quad\quad\quad\quad\quad COO^-$$

In these various groups $R_2$ is as defined above and represents advantageously a $-SO_3^-$ group and n is a number from 1 to 4, preferably 1.

Generally, the substitutions of the B, C and D units occupy essentially the 2 position of the glucosyl basic unit. The derivatives in which these substitutions open from other positions as well as optionally the 2 position, come however within the scope of the invention.

In the same way, the invention relates to the derivatives in which part of the $-OH$ groups of the glucosyls are in the form $-OR_2$.

By preparing a whole range of derivatives, Applicants have been able to demonstrate that the anticoagulant activity becomes very low when the ratio of the B units is less than about 35%. This is the same for the total absence of D units.

Generally, for a proportion of B units of the order of 40 to 50%, an increase in anticoagulant activity is observed with that of the number of D units and an anti-complementary activity substantially as high as that of heparin.

Derivatives of this type contain about 9 to 12% of D units thus having antithrombic activity which can reach 300 to 400 uT/mg for the relatively high molecular weights, higher than about 40,000. These values are lower of about 20 to 100 uT/mg or less with lower molecular weights of about 10,000. Such products have an anti-complementary activity of the order of 1 to 10 $\mu g/10^7$ EAC 4b 3b BbP.

Said values are measured according to the methods given in the examples.

The antithrombic activity is lower of the order of 1 to 5 uT/mg and the anti-complementary always higher of the order of 10 $\mu g/10^7$ EAC 4b3b BbP in the derivatives possessing a lower percentage of D units than about 4% the proportion of B units being from 40 to 50%.

A particularly preferred category of derivatives of the invention comprises derivatives of dextran including the following A, B, C and D units:

A

B

C

D in the proportions given above.

According to the invention there is also provided a process for preparing the above defined dextran derivatives.

According to this process, a dextran chain formed from unsubstituted A units is employed and successively the B, C and D units are developed these units being each obtained from that prepared previously in the order indicated.

The development of these different units on the dextran chain advantageously comprises the following steps, namely:

the reaction of a dextran with a derivative of the formula:

X(CH$_2$)$_n$—R—COOH in which X represents a reactive group capable of establishing a glucosylation link with a —OH group of glucosyl unit, which results in the formation of B units, The reaction of the dextran containing the A and B units with a derivative of formula in which R$_1$ is as defined above in order to obtain the fixation through an amide bridge of the substituted aryl group with the radical coming from the substituent chains of the B units, which permits the introduction of C units onto the chain, introduction of anions such as SO$_3^-$ on the aryl groups of the C units to obtain the D units, fractionation, optionally of the dextran derivatives, in order to eliminate the derivatives having a molecular weight less than 5000.

The separation of the dextrans can be carried out first, followed by the steps mentioned above.

Each of the above steps is optionally repeated until the production of the desired portion of units on the chain.

For developing B units there is advantageously made to react with dextran a reactive derivative such as a halogenide, more especially for reasons of availability, a chloride.

The substitution reaction is carried out in a basic medium under the conditions enabling degradation of the dextran chain sensitive to hydrolysis to be avoided.

In this respect, the basic reaction mixture containing the dextran is brought to a temperature of the order of 0° C. or below particularly —4° C. to +5° C.

After addition of the reactive derivative, the mixture is brought to a temperature above ambiant, and which can reach about 70° C.

Preferably, the process follows a temperature gradient, by making the room temperature increase gradually to about 55° C. As a result there is a yield of about 50% for one step, reaching practically 100% in two steps.

Due to the checking of the temperature, it is possible to have a variation of the substitution yield as desired. It is thus possible to obtain carboxylic ratios of 40 to 60% as well as 80% in one step, and practically 100%, even higher in two steps.

A large range of products having the desired properties is then available.

This modulation has interest considering that when it is desired to provide products endowed with high anticoagulant properties, it is preferable to have a lower proportion of B units, whilst this proportion must be higher to increase the anticoagulant activity of the derivatives.

The ratio of the concentration of reactive derivative to that of dextran is advantageously 1.9 to 3.5.

According to the method of recovery of the products by precipitation, the pH is lowered to a neutral pH.

The products are precipitated by means of a a solvent particularly an alcoholic solvent such as methanol.

When the chain R in the B units represents a —CO—NH—(CH$_2$)$_{n'}$ group, advantageously the products are obtained from B units substituted by a —O—(CH$_2$)$_n$—COO$^-$ chain by reaction with the corresponding amino acids.

The step of forming the C units comprises the coupling of derivatives of the formula with the substituent chain of the B units. Advantageously a coupling agent in an acid medium at room temperature is used.

These are coupling agents such as those mentioned in IBF reactives "Practical guide for use in affinity chromatography", 1979, p. 34–37, especially N-ethoxycarbonyl-2-ethoxy-1,2dihydrocholine (EEDQ), carbodiimid or N-isobutoxycarbonyl-2isobutoxy-1,2 dihydroquinoline (I.I.D.Q.).

In a modification enabling the reaction to be carried out with a high yield, namely about 10% of substitution, the mixed anhydride of the dextran is prepared by reaction an alkylchloroformate particularly an alkyl or isobutylchloroformate and a compound capable of forming an hydrochloride with HCl, such as triethylamine, N-methyl morpholine or similar. This activation step is carried out preferably at a temperature below 0° C. and even −15° C. This reaction takes place very rapidly in some minutes then the coupling is effected at low temperature.

The ratio of the concentration of the derivative to be coupled to that of the substituted dextran is advantageously of the order of 2 and that of the chloroformate with respect to the dextran about 1.

The dextran chains thus obtained are reacted with a reactive derivative containing $R_2$ and enabling $R_2$ to be fixed on the aryl nucleus of the chains of B.

Substitution by the groups $SO_3^-$ is advantageously effected by means of chlorosulfonic acid in dilute conditions in order to avoid the degradation of the dextran chain. This step is carried out in heterogeneous phase and the product is recovered, washed and dried.

In the course of this step, it is possible to substitute up to one half of the aromatic rings of the C units.

The operation is renewed if necessary until the production of the desired degree of substitution.

For biological uses, substituted dextran so-obtained is washed and then preserved in freeze-dried form.

By means of this process, it is possible to prepare synthetically, a range of dextran derivatives having the advantage of being soluble, in very variable proportions of substituted units, and these proportions can be selected according to the desired properties.

The biological activity of the dextran derivatives defined above were studied with respect to various ways particularly on certain proteins of coagulation, in particular, thrombin, and on the complement system.

The results obtained show that the activity of these derivatives with respect to thrombin depends on the percentage of B and D units.

This activity appears for a ratio of B units higher than 35%, more especially than 40% and increase with the percentage of D units. This activity seems therefore to result from a cooperative effect between the B and D substituent chains.

Examination of the isomolecular fractions of derivatives of the invention has shown a very distinct increase in the thrombin inhibiting activity with molecular weight.

Study of their action on the plasma proteins of the complementary system has demonstrated a strong power of inhibition with respect to the action of the $C_3$ alternate converse.

In the presence of blood, these products are thus capable of resulting, just as heparin, in a reduction in the hemolysis and a decrease in the inflammatory response of the organism.

The interest of these derivatives is further increased by reason of their good tolerence.

Toxicity tests have been carried out on mice of about 20 g by intravenous injection of 0.5 ml per mouse, of a solution of 40 mg/ml of the dextran modified according to the present invention in isotonic NaCl solution. These tests have demonstrated the total innocuity of the products according to the present invention: no reaction neither during injection, nor during the 14 days following the injection, was observed.

Taking into account their properties, these derivatives are particularly suitable for use as blood plasma substitutes more especially as expanders with the advantage with respect to dextrans then of reducing the risks of hypersensitivities observed in certain cases.

The invention therefore relates also to biomaterials useful as blood plasma substitutes and expanders based on the above dextran derivatives in about 5% to 15% solution, particularly about 10% in a saline medium.

These expanders are used, for example, at the rate of 1.5 to 2 l/day.

As shown in the example, dextran derivaties of the invention, particularly those having a high molecular weight, especially above 50,000 have anticoagulant activity a above 300, which can reach 400 or higher. Preferred derivatives have about 40% of units B, about 20% of units D and about 40% of units A.

The invention relates also to the pharmaceutical composition comprising the dextran derivatives of the invention and preferably those defined above in admixture with pharmaceutically acceptable carriers Particularly, it concerns, the compositions in which the pharmaceutical vehicle is suitable for the administration by oral, rectal route or which are injectable. Such solutions contain 10 to 50 mg by portion.

The injection, carried out by subcutaneous, intraveneous or perfusion route can be repeated 2 or 3 times/day depending on the patient and of the results of the biologicals tests.

These derivatives also constitute valuable supports for the fixation of different substances with therapeutic activity.

DESCRIPTION OF PARTICULAR EMBODIMENTS

The invention is explained in more detail in the examples that follow relating to the preparation of dextran derivatives and to the study of their biological activities.

EXAMPLE 1

Preparation of dextran derivatives comprising the following units A, B, C and D

-continued

A sample of dextran of molecular weight higher than 8000, the separation having been carried out by low pressure liquid chromatography, was subjected to the following steps 1 to 5:
(1): carboxymethylation by means of monochloroacetic acid
(2): fixation of benzylamine by coupling of this derivative
(3): sulfonation of the aromatic nuclei of the benzylamine
(4): washing and conditioning.

1st Step: Carboxymethylation of the Dextrans

This step is inspired by the work of F. ANTONINI & Coll. (Giorn. Biochi. 14, 88, 1965).

Into a 1 liter flask provided with a stirring system and immersed to two-thirds in a bath ice+salt (−4° C.)|, are dissolved 48.6 g of dextran (0.30 Mole) in 400 ml of soda (2.4 Moles). It is left to stand with stirring at −4° C. for 20 minutes.

Into the flask, is introduced little by little (duration of the introduction 10 minutes) 100 g of ClCHCOOH (1.05 Moles).

The temperature is brought to 70° C. and this temperature is maintained and with stirring for 20 minutes.

It is cooled again by immersing the flask to two-thirds in an ice bath.

The pH which shows a value close to 11 is adjusted to 7 by the addition of acetic acid.

The product is precipitated by means of 3 liters of methanol then it is washed with methanol and it is dried in an oven under vacuum at about 40° C.

By this method, about 30% of the dextran rings are substituted, without degradation of macromolecular chains. The more extensive substitutions are obtained by repeating several times (n times) this operation according to Table I below:

TABLE I

| n (carboxymethylation number) | % of carboxymethylated dextran units |
|---|---|
| 1 | 30–32 |
| 2 | 45–50 |
| 3 | 60–65 |
| 4 | 75–80 |
| 5 | 90–98 |

2nd Step: Fixation of the Benzylamine

This step is inspired by the work of P. V. SUNDARAM (Biochem. Biophys. Res. Comm. 61, 717, 1974).

In a 2 liter flask, are dissolved with stirring at ambiant temperature 40 g of carboxymethyldextran with 90% of carboxymethylated dextran units (prepared in the course of the first step) in 290 ml of water.

The pH is adjusted to about 3.5 with 1N hydrochloric acid. 89 g (0.360 Mole) of N-ethoxycarbonyl-2-ethoxy-1,2-dihydroquinoline (E.E.D.Q.) of the formula:

dissolved in 710 ml of absolute ethanol,

It is kept under stirring for a half hour.

40 ml of benzylamine (0.36 Mole) are added and it is left to stand under stirring overnight.

After evaporation of the mixture almost to dryness, the dextran is precipitated by means of 2 liter of methanol, it is washed with methanol and dried in the oven under vacuum at 40° C.

3rd Step: Sulfonation of the Aromatic Nuclei of the Benzylamine 12 g of product obtained in the course of the 2nd step and comprising 1 mMole/g of benzylamine are dispersed with stirring in 240 ml methylene chloride.

Slowly 2.4 ml of chlorosulfonic acid (0.036 Mole), are added, the reaction mixture is left under stirring overnight, it is filtered, washed with ethanol then dried in the oven under vacuum under 40° C.

By this method, up to about one half of the aromatic rings of the benzylamine are substituted.

To obtain the desired degrees of sulfonation, the operation is repeated several times.

4th Step: Washings and Conditioning

The product obtained at the end of the 3rd step is dissolved in an aqueous solution of soda and the pH is kept at 8 for 2 hours.

It is then washed with water, equilibrated to pH 7.35 with Michaelis buffer, then rewashed with water. All the operations are carried out by using the ultrafiltration method (semi-permeable) membranes with suitable cut level).

EXAMPLE 2

Carboxymathyletion and coupling of the benzylamine according to an alternative embodiment carboxymethylation 30 g (0.185 moles) of dextrane having $\overline{M}m$ of about 40,000 are dissolved in 246 ml of soda 6N (1.48 mole) and submitted to stirring during 20 mn to 61.2 g of $ClCH_2COOH$ (0.647 mole) are then introduced while maintaining the temperature at 20° C.

The reaction mixture is then heated to reach 55° C. 20 mn later.

The reaction is maintained during a time varying from 0 to 60 mn depending on the desired substitution degree (25 to 85% of carboxyldextran).

It is also possible to check the carboxymethylation yield by fixing time t2 at 40 mn and by varying the ratio of the monochloracetic acid amount to the dextrane units amount according to $1 \leq R \leq 3.5$.

In a double jacket reactor connected to a cryostat, 1 g of carboxymethyldextrane (6.17 mmoles) are dissolved into 2 ml of water. The mixture is acidified at about ph 3.5 with concentrated HCl. 16 ml of dimethylformamid are added very slowly while keeping the pH at about 3.5. The solution is then brought to $-15°$ C. A volume V1 (0.44 ml) of N-methylmorphodine and a volume V2 (0.52 ml) of isobutylchloroformate are then added. One minute later, volume V3 (0.49 ml) of benzylamine are introduced.

The reaction is: aintained under stirring during a time t1 (5 to 60 mn) at $-15°$ C. and the temperature is raised to 20° C. The reaction mixture is submitted to stirring 1 hour.

After evaporation under vacumn, the product is precipitated into 500 ml of methanol, filtrated on a fritted glass. The recovered product is put into water, ultrafiltrated on a calibrated membrane.

The product is finally freeze-dried.

The ratios of benzylamine fixed on the carboxylic chains vary between about 1 and 15% in onestep

EXAMPLE 3

By carring out the process of example 1 or 2, a series of dextrane derivatives have been prepared with various substitution ratios.

Such derivatives are reported in table 1 below which comprises the corresponding compositions and the average molecular masses in number.

TABLE 1

| | | $\overline{Mn}$ | | Composition | | |
|---|---|---|---|---|---|---|
| | Reference | Theoretical value | tonometry measurement | B % ± 1 | C % ± 1 | D % ± 1 |
| 1 | (Dextrane) | 4900 | | 0 | 0 | 0 |
| 2 | ⎫ | 5600 | 5300 | 30 | 0 | 0 |
| | ⎬ C.M. Dextrane | | | | | |
| 3 | ⎭ | 7200 | 7000 | 95 | 0 | 0 |
| 4 | | | | 51 | 14 | 0 |
| 5 | | 6714 | 7100 | 37 | 21 | 0 |
| 6 | | | | 37 | 11 | 9 |
| 7 | | 6721 | 6930 | 37 | 15 | 5 |
| 8 | | | | 37 | 15 | 6 |
| 9 | | | | 70 | 7 | 1 |
| 10 | | | | 71 | 7 | 1 |
| 11 | | | | 47 | 1 | 3 |
| 12 | | 6628 | 6670 | 40 | 12 | 3 |
| 13 | | | | 40,5 | 4 | 4 |
| 14 | | | | 40,5 | 4 | 10 |
| 15 | | | | 43 | 0 | 15 |
| 16 | | | | 45 | 0 | 4 |
| 17 | | | | 60 | 14 | 5 |
| 18 | | | | 76 | 0 | 4,5 |
| 19 | | | | 58 | 5 | 6 |
| 20 | | | | 67 | 0 | 5 |
| 21 | | 6140 | 5980 | 45 | 0 | 5 |
| 22 | | | | 50 | 3 | 10 |
| 23 | | | | 43 | 4 | 11 |
| 24 | | | | 49 | 1 | 12 |
| 25 | | | | 68 | 4 | 12 |
| 26 | | | | 71,5 | 0 | 10 |
| 27 | | | | 75 | 0 | 14 |
| 28 | | | | 45 | 0 | 14 |

EXAMPLE 4

Study of the thrombin time, of the reptilase time and of the anticoagulant activity of the derivatives of the invention 3.1: thrombin time and reptilase time.

Method:

Thombin time (TT) and reptilase time (RT) are measured.

The thrombin time corresponds to the time of formation of the clot after addition of the thrombin to a plasma specimen or a fibrinogen solution.

The reptilase time enables a check to be made that the capacity of converting fibrinogen to fibrin is not modified in the presence of the dextran derivative.

These measurements are determined automatically at 37° C. by the means of a Dade DCl coagulometer, by operating as follows:

0.2 ml of platelet-poor plasma (PPP) or fibrinogen (6 g/l) is incubated at 37° C. with 0.1 ml of Michaelis buffer containing in a suitable concentration the dissolved dextran derivative.

The duration of incubation is 5 min.

0.1 ml of solution of thrombin (in a Michaelis buffer) or of reptilase (in distilled water) is added and the time of the appearance of the clot is measured (TT or RT).

The control time is determined with a volume of buffer free from a dextran derivative.

Figure 1:
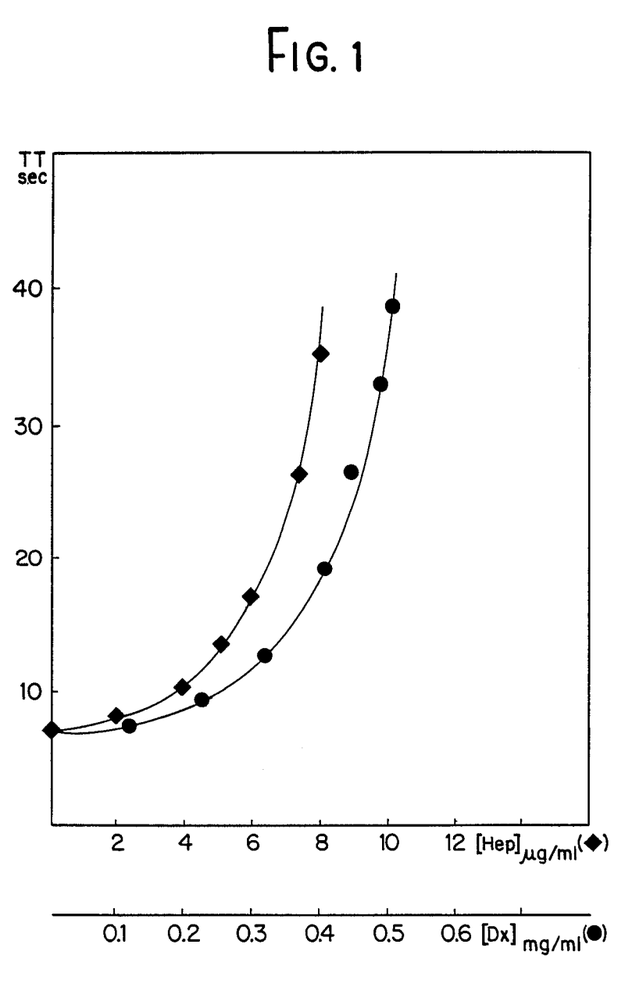

The development of the TT on plasma as a function of the concentration of the polymer appears parallel with that observed with heparin as shown in FIG. I. In this Figure has been indicated the variation of the TT as a function (1) of a derivative containing 14% of D unit and 45% of B unit (curve ●), (2) of a heparin (curve ◆).

The heparin used has a USP activity of 173 iu/mg and a molecular weight to 10,700 daltons.

results

In Table 2, are reported the thrombin times on plasma and fibrinogen as well as the reptilase time, obtained with the various dextran derivatives (percentages of B, C and D units of these derivatives are given in Table 1).

tions testify in favor of the participation of antithrombin III in this mechanism as in the case of heparin.

3.2 Anticoagulant Activity:

The anticoagulant activity (a) is determined from thrombin times of the PPP in the presence of various polymer concentrations.

The activity a is defined as being the number of thrombin units inactivated per milligram of product (uT/mg).

This amount of inactivated thrombin is determined from a calibration curve.

Under the same conditions, commercial heparin has an activity coefficient a equal 4000 uTH/mg.

results

In Table 3 below are reported the values of the anti-

TABLE 2

Thrombin times (TT) on plasma and fibrinogen as well as reptilase times (RT) of the derivatives of dextran.

| Reference (See Table 1) | Initial Concentration (C) of polymer mg/ml | Thrombin Time: TT sec ± 1 On plasma (Initial Concentration of Thrombin 20 u NIH/ml) Control: 8 | On Fibrinogen 6 g/l NaCl 0.145 M Control: 8 | Reptilase Time RT (sec ± 1) on plasma Control: 18 |
|---|---|---|---|---|
| 1 (Dextran) | 50 | 9 | | |
| 2 } CM Dextran | 50 | 8 | | |
| 3 | 50 | 9 | | |
| 4 | 50 | 9 | | |
| 5 | 50 | 8 | 22 | 20 |
| 6 | 35 | 20 | 28 | 18 |
| 7 | 50 | 18 | | |
| 8 | 40 | 19 | | |
| 9 | 36 | 21 | | |
| 10 | 33 | 18 | | |
| 11 | 20 | 19 | 15 | 18 |
| 12 | 15 | 21 | | |
| 13 | 10 | 18 | | |
| 14 | 6 | 20 | | |
| 15 | 2 | 18 | | |
| 16 | 1,5 | 21 | | |
| 17 | 1,8 | 20 | | |
| 18 | 1,6 | 20 | 9 | 18 |
| 19 | 1,8 | 21 | | |
| 20 | 1,6 | 21 | | |
| 21 | 1,5 | 21 | | |
| 22 | 1,5 | 19 | | |
| 23 | 1,25 | 20 | 8 | 18 |
| 24 | 1 | 22 | 8 | 18 |
| 25 | 1 | 20 | | |
| 26 | 0,8 | 21 | | |
| 27 | 0,3 | 20 | | |
| 28 | 0,3 | 22 | | |
| 29 | 1 | 19 | | |
| 30 | 1 | 23 | | |
| 31 | 0,6 | 20 | | |
| 32 | 0,5 | 22 | | |
| Heparin 173 IU/mg | $6 \cdot 10^{-3}$ | 18 | | |

It is observed that the reptilase time is not prolonged in the presence of polymer and hence the fibrinogen is not altered. This invariability of reptilase times permits correlation of the extension of thrombin time on plasma to an anticoagulant activity.

Thrombin times on fibrinogen are of the order of that of the controls when the concentrations of the dextran derivatives are low.

On the other hand, when these concentrations are high there is observed a slight prolongation of these times which could manifest the possibility of a direct action of the polymer on the thrombin. These observacoagulant activity a in uT/mg for the derivatives concerned in Table 2.

TABLE 3

| Reference | Anticoagulant activity $a$(uT/mg) |
|---|---|
| 1 (Dextrane) | 0 |
| 2 } C.M. Dextrane | 0 |
| 3 | 0 |
| 4 | 0 |
| 5 | 0 |
| 6 | 1 |

TABLE 3-continued

| Reference | Anticoagulant activity $a$(uT/mg) |
|---|---|
| 7 | 1 |
| 8 | 1 |
| 9 | 1 |
| 10 | 1 |
| 11 | 2 |
| 12 | 3 |
| 13 | 4 |
| 14 | 6 |
| 15 | 14 |
| 16 | 15 |
| 17 | 16 |
| 18 | 17 |
| 19 | 18 |
| 20 | 18 |
| 21 | 20 |
| 22 | 22 |
| 23 | 23 |
| 24 | 29 |
| 25 | 31 |
| 26 | 40 |
| 27 | 65 |
| 28 | 70 |

Figure 2A:
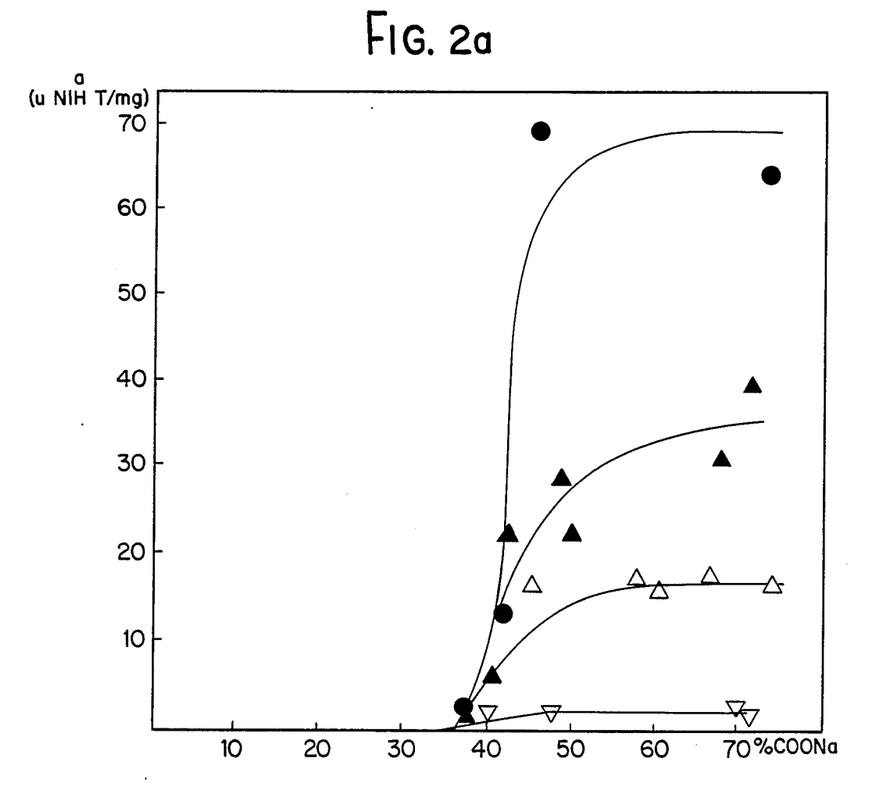
Figure 2B:
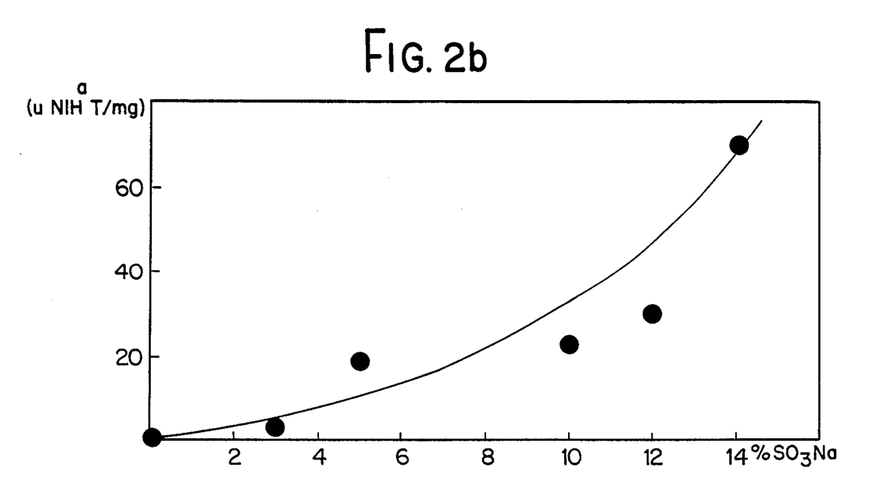

Variation of the anticoagulant activity a as a function of the respective proportions of B and D units For the products 1 to 28 the activity a has been reported in FIGS. 2a and 2b as a function of the proportion of B units bearing carboxymethyl groups or sulfonated D units.

FIG. 2a corresponds to the variation of the activity a of the dextran derivatives of starting Mp 10,500 as a function of the proportion of B units with a proportion of D units of 15±1 (curve ●), 11±1 (curve ▲) 6±1 (curve Δ) and 2±1 (curve ▽).

FIG. 2b corresponds to the variation of activity a of the dextran derivatives used as a function of the proportion of D units, the proportion of B units being 47, 5±2,5%.

Examination of these results shows that an antithrombic activity is obtained when the products contain at least 35% of B units.

A rapid increase in the value a will also be noted, beyond the threshold of appearance of antithrombic activity (FIG. 2a).

This increase in a appears all the stronger the proportion of units of the dextran support bearing sulfonate groups is higher (FIG. 2b).

Influence of the molecular weight

With the object of study the correlations between the molecular weight and anticoagulant activity, a very polydispersed derivative ($\overline{MW}=15600$, $\overline{Mn}=7400$, $\overline{MW}/\overline{Mn}=2,1$), moderately active of dextran (a=8 uT/mg) was fractionated as follows: filling of the column: a gel previously washed and expanded in double distilled water at 20° C. for ten hours, before being introduced into a glass column (LKB) 1 m long and 2.5 cm internal diameter, was used.

eluant: 0.2M aqueuse solution of NaCl drawn at 25 ml/h by a "Vario Perpex" (LKB) roller pump
charge: 100 mg of product in 5 ml of eluant
volumes collected: 8 ml
detection of the concentration of the eluted solution by UV spectroscopy (280 nm).

After passage over this column, the product was fractionated according to its molecular weight into 5 fractions. (It was verified by chemical assay that the separation was effected purely as a function of the weight).

The weight of each fraction was determined by high pressure liquid exclusion chromatography (90 bars) on a "Merck Lichrospher" column 100 diol., in an aqueous 0.2M NaCl medium, and after calibration of the column.

The anticoagulant activity a of each fraction is summarized in Table 4a below:

TABLE 4a

| Fraction | Weight | Activity a (uTh/mg) |
|---|---|---|
| 1 | 27 000 | 20 |
| 2 | 19 0000 | 14 |
| 3 | 15 000 | 8 |
| 4 | 8 000 | 6 |
| 5 | 6 300 | 3 | a similar fractionation is carried out on a dextran having a molecular weight of about 40,000, using a column of 5 cm/40 cm, a gel of Sephadex S 300 Superfine, and filing with 500 mg in 10 ml of eluent; The five fractions obtained are reported in table 4b below:

TABLE 4b

| Fraction | Mass | Activity a (uT/mg) |
|---|---|---|
| 1 | 85 000 | 300 |
| 2 | 52 500 | 285 |
| 3 | 39 500 | 270 |
| 4 | 27 500 | 154 |
| 5 | 14 500 | 11 |

In the domain of molecular weights concerned it is observed that anticoagulant activity increases with the molecular weight.

EXAMPLE 5

Study of the action of derivatives of the invention on the proteins of the contact phase of coagulation The proteins relating to the contact phase are those which are activated in contact with a surface other than the endothelium and are responsible, at least in part, for the activation of the other factors of coagulation.

Kallikrein, an enzyme coming for activation of the contact phase, increases the activation of this system.

There are reported below the results obtained with the dextran derivatives according to the invention from the point of view of their action on the proteins of the contact phase.

Method

The development test of activation of the contact phase consists of determining the enzymatic activity of the kallikrein. The latter is demonstrated by an amidolysis of a specific chromogenic substrate of the enzyme (substrate S2302 marketed by Kabi). The speed of liberation of one of the products of the hydrolysis, paranitronaniline (pNA) is followed by spectrophotometry at 405 nm.

The increase in the optical density per unit time at 405 nm is proportional to the enzymatic activity of the kallikrein.

The response of this test is global since it does not permit analysis separately of the differnt steps of activation of the contact phase.

Activation by the derivatives of dextran was analyzed as a function of their concentration and, on the other hand, as a function of their nature and their composition in substituent.

According to the results obtained the amplitude of activation of the contact system appears as an increasing function of the concentration of the active derivative of the dextran.

The activator power of the polymers with respect to the contact phase appears to develop as a function of the nature and of the composition in substituents similarly to their anticoagulant acitivity: An increase in activity appears beyond a certain proportion of B units and seems all the more marked as the proportion of D units is higher.

EXAMPLE 6

Study of the action of the dextran derivatives of the invention on the complementary system The action of dextran derivatives of variable compositions on alternate $C_3$ convertase, was studied, i.e. the enzymatic complex which can cleave the protein $C_3$, the protein of the alternate path of the complementary system.

In the presence or in the absence of specific antibodies, the complementary system takes part in the systems of recognition or defense of the host with respect to infectious agents or foreign cells.

Method

Erythrocytes bearing C3b fragments (small fragments released by cleavage of $C_3$) and called more precisely EA C4b 3b, are separated from sensitized sheep erythrocytes (EA) according to the procedure described by the M-D-Kazatchkine and coll. J. Cli. Invest. 67, 223, 1981.

The erythrocytes were then placed in the presence of amounts of proteins and B, D, P stabilizer sufficient to obtain a "$C_3$ amplifying convertase" site per cell endicated by EA C4b 3b Bb P. These sites activate the effective route of the complement comprising the plasmatic proteins $C_5-C_6-C_7-C_8-C_9-$ and cause hemolysis of the erythrocytes which release hemoglobin.

0.1 ml fractions of this suspension are taken up and added to 0.1 ml DGVB++ buffer (Veronal buffer+0.1% of gelatin and containing 0.15 mM of Ca++ and 0.5 mM of Mg++, diluted to ½ with a 5% dextrose solution containing 0.15 mM Ca++ and 0.5 mM Mg++) alone or containing adequate amounts of modified dextran according to the present invention.

The mixture is incubated 30 minutes at 30° C. with stirring.

0.3 ml of rat serum diluted to 1/20th in GVB-EDTA buffer (Veronal buffer+0.1% of gelatin containing 0.04M EDTA) was added.

The C3 convertase sites formed are developed by 60 minutes incubation at 37° C. with shaking.

The reaction is arrested by adding 1.6 ml of 0.15M NaCl.

The tubes are centrifuged and the intensity of the lysis is determined by reading of the supernatants at 412 nm by analysis on the spectrophotometer.

The number of hemolytic sites per cell is calculated.

Inhibiting activity

The inhibiting activity of the product tested is expressed as a percentage of inhibition of formation of convertase with reference to the control tube where the convertase has been formed in the absence of modified dextran according to the present invention.

This activity is expressed by weight of product (at constant volume) necessary for 50% inhibition of formation of the convertase.

This activity varies according to the units.

In table 5 below are reported the results obtained with the dextran derivatives of table 1

TABLE 5

| Reference (No. of sample Of Table 1) | Anticomplementary Activity $\mu g/10^7$ EAC 4b 3b Bb P |
|---|---|
| 1 (Dextran) | ∞ |
| 3 (CM Dextran) | 80 |
| 4 | 60 |
| 12 | 60 |
| 16 | 13 |
| 20 | 11 |
| 10 | 21,5 |
| 7 | 60 |
| 17 | 10 |
| 6 | 45 |
| 23 | 7,5 |
| 22 | 4 |
| 25 | 4 |
| 26 | 3 |
| Heparin 158 IU/mg | 1 |

Examination of these results shows that the anticomplementary activities of the derivatives of dextran reach values which are of the same order and even for certain derivatives higher than that of heparin.

Figure 3:
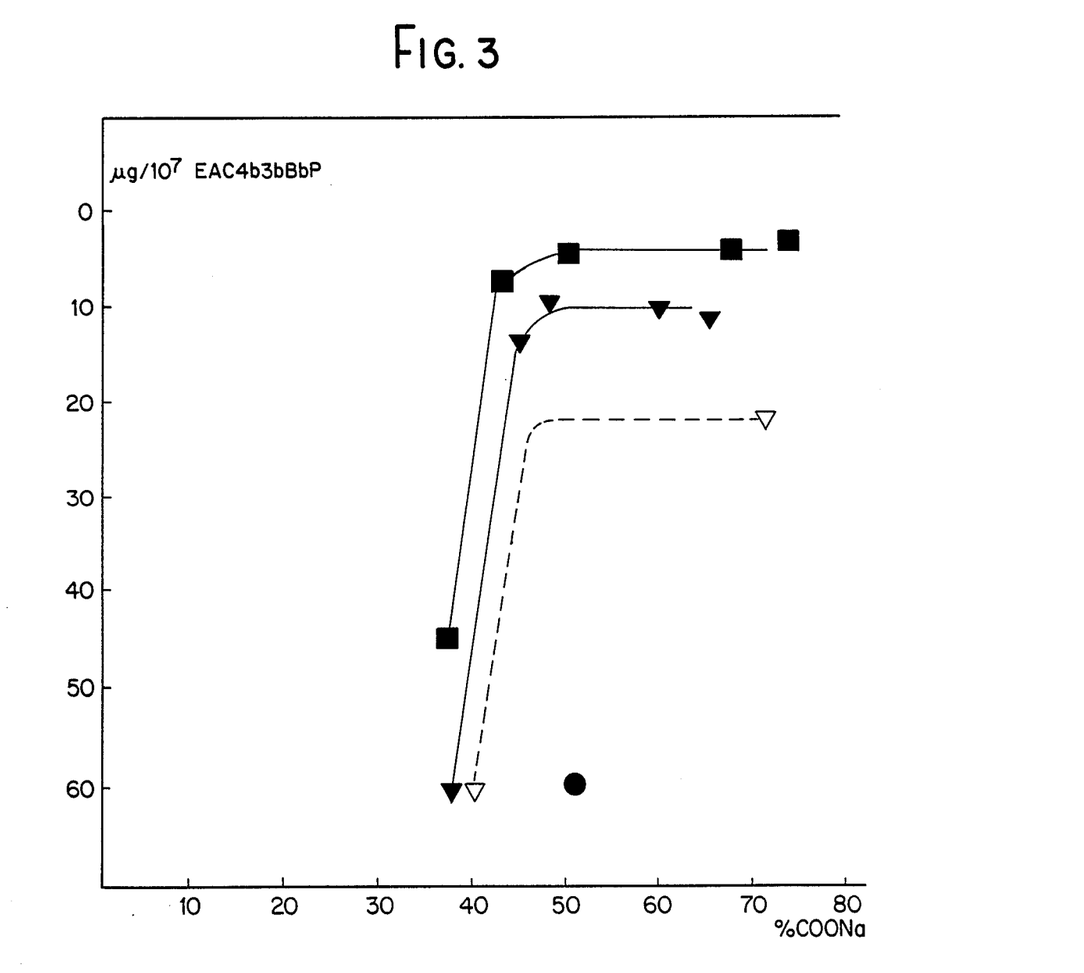

In FIG. 3, is shown that the development of the anticomplementary activity of the derivatives of dextran as a function of their chemical compositions for ratios of the B units varying from 10 to 90% and ratios of D units equal to:

9–12%:curve u

4–5%:curve v

2–3%:curve w 0%:O

It is observed that the inhibiting activity increases at the same time as the increase in the ratio of the D units for a ratio of B units of 40–50%, the increase in the ratio B units beyond this value not bringing an improvement. It is to be noted also that the change as a function of the B and D units of the anticomplementary activity is very close to that of the anticoagulant activity a.

It will noted that the derivatives with low ratios of D units already have a considerable anticomplementary activity whereas their anticoagulant activity is very low.

It will be noted, in addition, that the presence alone of the C units induces a slight anti-complementary activity whilst it does not result in any anticoagulant effect.

Figure 4:
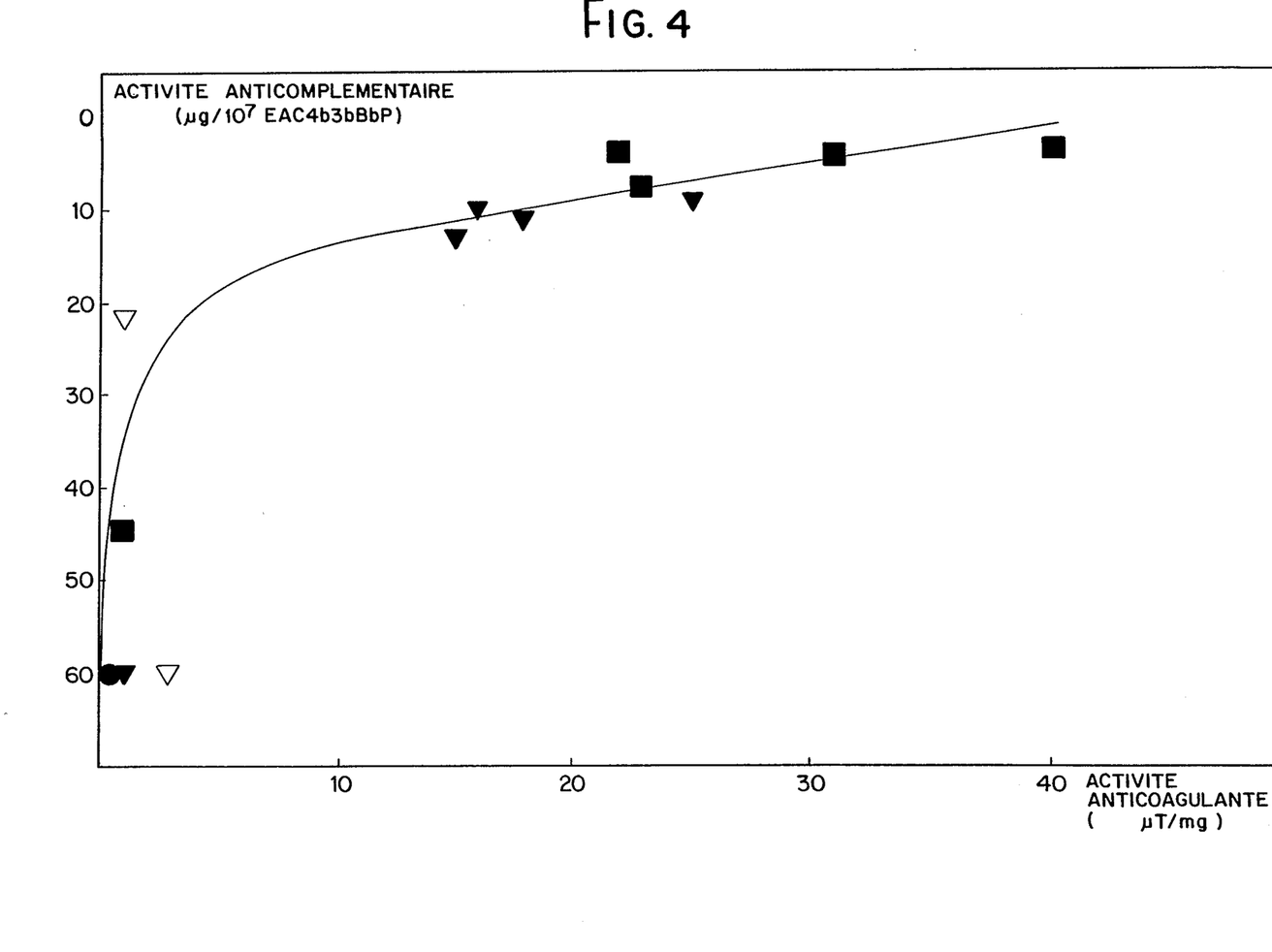

In FIG. 4, is reported the curve obtained by studying the correlation between the anticomplementary activity and the anticoagulant activity of the above derivatives with symbols ■, ▼, ●, and ▽ corresponding respectively to dextrans containing 9 to 12% of D units, 4 to 5%, 0% and 2 to 3%.

This figure demonstrates the possibility of obtaining the producrs endowed with high anticomplementary activity and low anticoagulant activity.

We claim:

1. Polymers of dextran having a molecular weight higher than 5000 daltons comprising statistically, glucosyl units A with 1,6 linkages, of the formula:

at least 35% of B units, consisting of units A substituted by a radical —O—(CH$_2$)$_n$—R—COO$^-$ in which R represents a single bond or a —CO—NH—(CH$_2$)$_{n'}$—, n is a number from 1 to 10 and ' is a numbver from 1 to 7, and at least 3% of D units, consisting of units A substituted by a chain with a group of structure in which:

—R$_1$ represents a single bond, —CH$_2$— group, or a group,

R$_2$ represents a physiogically acceptable anion of an inorganic or organic salt, and an inorganic or organic salt, and n is as defined above.

2. The polymers of dextran of claim 1 wherein B is at least 40%.

3. The polymers of dextran of claim 1 wherein R$_2$ is SO$_3^{31}$.

4. The polymers of dextran of claim 1 wherein B is at least 40% and R$_2$ is SO$_3^{31}$.

5. The polymers of dextran of claim 1 which further comprises C units consisting of A units substituted by radicals of the structure:

in which R$_1$ and n are as defined in claims 1.

6. The polymers of dextran of claim 2, wherein A and B units represent at most 60% of the total number of units.

7. Polymers of dextran having the following A, B, C and D units

-continued wherein A and C units represent at most 50% and B and D being as defined in claim 1.

8. The polymers of dextrans of claim 1 wherein the B units are substituted by —O—CH$_2$—COO$^-$.

9. A process for making the dextran polymers of claim 1 comprising in combination bringing to a temperature of about —4° to +5° C. and reacting a dextran with units A of the formula with a carboxylic acid of the formula:
X(CH$_2$)$_n$—R—COOH, in which X represents a group which reacts with the —OH group of a glycosyl unit A in a ratio of carboxylic acid and dextran of 1.5 to 3.5, and bringing the temperature to between about ambient and about about 70° C., whereby there are formed B units consisting of A units substituted by a radical —O—(CH$_2$)$_n$—R—COO$^-$, R and n being as defined above, then reacting the dextran containing the A and B units with a derivative of formula in which R$_1$ is as defined above which causes the introduction of C units consisting of A units substituted by a chain with a group of structure:

with n, and R$_1$ as defined above, and reacting the C units with an organic or inorganic salt, whereby there is obtained the D units in combination with the A, B and C units.

10. The process according to claim 9 comprising the fractionation of the dextran polymers, thereby eliminating the derivatives having a molecular weight less than 5000 daltons.

11. The process according to claim 9 wherein the units B are prepared by reacting an halogenide with the dextran consisting of units A.

12. The process according to claim 9 wherein the reaction mixture is brought to a temperature of about 0° C.

13. The process of claim 9 wherein after the mixture is brought to a temperature above ambient, the temperature is gradually raised to between about ambient ot about 55° C.

14. The process according to claim 9 wherein the dextran polymer with the A and B units is recovered by precipitation with an alcoholic solvent and by lowering the pH to about neutral.

15. The process according to claim 9 wherein the units C are prepared by coupling the units B with a compound of formula in the presence of a coupling agent.

16. The process according to claim 9 wherein the units C are prepared by coupling a mixed anhydride of the dextran with A and B units with a reactive compound containing R$_2$ which results in the formation of a radical wherein n, R$_1$ and R$_2$ are as defined.

17. The process according to claim 16 wherein the mixed anhydride of dextran is obtained by reacting an alkyl formate with an amine which yields a hydrochloride with HCl, at a temperature lower than 0° C., then coupling the resulting compound with the units B of the dextran.

18. A method for the preparation of plasma substitutes or expanders which comprises making an aqueous solution of a polymer which has the formula of claim 1.

19. A method for the preparation of plasma substitutes or expanders which comprises making an aqueous solution of a polymer of dextran which as the formula of claim 7.

20. A biological composition which comprises a polymer of dextran having a molecular weight higher than 5,000 daltons and comprising statistically
glucosyl units A with 1,6 linkages, of the formula:

at least 35% of B units, consisting of units A substituted by a radical —O—(CH$_2$)$_n$—R—COO$^-$ in which R represents a single bond or a —CO—NH—(CH$_2$)$_{n'}$—, n is a number from 1 to 10 and n' is a number from 1 to 7, and at least 3% of D units, consisting of units A substituted by a chain with a gorup of structure in which:
R$_1$ represents a single bond, —CH$_2$—group, or a —CH—CH$_2$—group,
R$_2$ respresents a physiogically acceptable anion of an inorganic or organic salt, and an inorganic or organic salt, and n is as defined above in a mixture with a biologically acceptable carrier.

21. The biological composition of claim 20 wherein the dextran polymer has the following A, B, C and D units 22. The composition of claim 20 which is a blood plasma substitute and expander.

23. The blood plasma substitute of claim 22 wherein the dextran polymer is in an aqueous concentration of about 5 to 15%.

24. The blood plasma of substitute of claim 22 wherein the solution is a saline solution.

25. The freeze-dried polymer of dextran of claim 1.

26. The freeze-dried polymer of dextran of claim 7.

* * * * *

UNITED STATES PATENT AND TRADEMARK OFFICE
CERTIFICATE OF CORRECTION

PATENT NO. : 4,740,594
DATED : April 26, 1988
INVENTOR(S) : MAUZAC ET AL

It is certified that error appears in the above–identified patent and that said Letters Patent is hereby corrected as shown below:

Col. 19, Claim 1, lines 14 and 15, "and ' is a numbver" should read --and n' is a number--.

Claim 3, line 41, "$SO_3^{31}$" should read --$SO_3^-$--.

Claim 4, line 43, "$SO_3^{31}$" should read --$SO_3^-$--.

Signed and Sealed this

Twenty-second Day of August, 1989

Attest:

- DONALD J. QUIGG

Attesting Officer     Commissioner of Patents and Trademarks